(12) United States Patent
Borresen et al.

(10) Patent No.: US 6,623,264 B1
(45) Date of Patent: Sep. 23, 2003

(54) UNIT FOR MAKING PRE-SHAPED ABSORBENT PADS FOR SANITARY ITEMS

(75) Inventors: Harald Borresen, Stokke (NO); Eligiusz Berdychowski, Tolvsrod (NO); Ivar Bjarne Mo, Tonsberg (NO); Carlo Trimani, Bologna (IT)

(73) Assignee: GDM S.p.A., Bologna (IT)

( * ) Notice: Subject to any disclaimer, the term of this patent is extended or adjusted under 35 U.S.C. 154(b) by 74 days.

(21) Appl. No.: 09/698,157

(22) Filed: Oct. 30, 2000

(30) Foreign Application Priority Data

Nov. 2, 1999 (IT) .......................... BO99A0586

(51) Int. Cl.[7] ............................................. B29C 43/06
(52) U.S. Cl. ................... 425/80.1; 425/81.1; 425/219; 425/504; 425/217; 264/113
(58) Field of Search ................. 425/217, 80.1, 425/81.1, 82.1, 83.1, 388, 504, 219; 264/112, 113, 119

(56) References Cited

U.S. PATENT DOCUMENTS

| | | | |
|---|---|---|---|
| 3,737,265 A | * 6/1973 | Schafer et al. ............... 425/140 |
| 4,005,957 A | 2/1977 | Savich ....................... 425/80.1 |
| 4,674,966 A | 6/1987 | Johnson et al. ............. 425/82.1 |
| 4,741,941 A | 5/1988 | Englebert et al. .............. 428/71 |
| 4,931,005 A | 6/1990 | Tanaka et al. .............. 425/83.1 |
| 5,145,351 A | * 9/1992 | Rossi ......................... 425/80.1 |
| 5,466,409 A | * 11/1995 | Partridge et al. ........... 425/83.1 |
| 5,620,712 A | 4/1997 | Nishino et al. ............. 425/80.1 |
| 5,762,844 A | * 6/1998 | Van Himbergen et al. . 425/80.1 |
| 5,919,178 A | 7/1999 | Widlund ..................... 156/276 |

* cited by examiner

Primary Examiner—Robert Davis
Assistant Examiner—Thu Khanh T. Nguyen
(74) Attorney, Agent, or Firm—Davidson Berquist Klima & Jackson, LLP

(57) ABSTRACT

A unit for making pre-shaped absorbent pads for sanitary items is equipped with a continuous conveyor belt with an operating branch which defines a line for pad forming and feed; the branch extends along a straight path, along which there are three successive stations for feeding absorbent material and a plurality of seats designed to accept and retain a given quantity of the absorbent material.

12 Claims, 3 Drawing Sheets

UNIT FOR MAKING PRE-SHAPED ABSORBENT PADS FOR SANITARY ITEMS

BACKGROUND OF THE INVENTION

The present invention relates to a unit for making pre-shaped absorbent pads for sanitary items.

In particular, the present invention relates to a unit of the above-mentioned type which can advantageously be used for the production of diapers, sanitary towels and similar items.

The following description refers, without limiting the scope of the invention, to units for making pre-shaped absorbent pads for diapers.

As is known, diapers contain an absorbent pad which is normally sealed between an inner permeable layer of spun-bonded material and an impermeable polyethylene outer layer.

In the past, absorbent pads for diapers were relatively thick and were obtained by cutting into sections a continuous web consisting of a collection of absorbent material, normally cellulose fiber. Then, in response to new market demands, diaper manufacturers began to make anatomically shaped diapers. This meant that the pads had to be shaped, according to the desired anatomical shape, before being sealed between the above-mentioned inner and outer layers.

For a lengthy period the best solution consisted in the use of a pad forming drum, the outside of which was equipped with a plurality of vacuum seats shaped according to the desired anatomical shape for the pad, said outer surface being fed with absorbent material. A forming drum of the above-mentioned type is known, for example, from U.S. Pat. No. 4,674,966.

However, in recent years, on one hand the market demand has been for diapers with pads that are increasingly thin and absorbent, and on the other, diaper manufacturers requested increasingly fast production units. This led to a gradual reduction in the depth of the shaped vacuum seats and, at the same time, an increase in the peripheral speed of the above-mentioned forming drums.

The reduction of diaper pad thickness to extremely low levels and the improvement in diaper absorption were made possible by using super-absorbent materials inserted, according to a multi-layer structure, between layers of the collection of cellulose fiber. An absorbent pad of the aforesaid multi-layer type is known, for example, from U.S. Pat. No. 5,919,178.

The increase in the peripheral speed of the forming drums is obtained by increasing both the angular velocity of rotation and the external diameter of the drums. The increase in the angular velocity was possible up to a speed limit beyond which it was found that the layers of super-absorbent material and collections of cellulose fiber, subjected to excessive centrifugation, tended to break up and penetrate one another. Moreover, the increase in external diameter made the forming drums increasingly bulky, heavy and expensive.

SUMMARY OF THE INVENTION

The aim of the present invention is to provide a unit for making pre-shaped absorbent pads for sanitary items, such as diapers, sanitary towels or similar products, with a relatively high production speed and, at the same time, free of the disadvantages indicated with reference to the prior art.

Accordingly, the present invention provides a unit for making pre-shaped absorbent pads for sanitary items. The unit comprises conveyor means defining at least one line for the formation and feed of said absorbent pads and at least one absorbent material feed station located along the forming and feed line. The conveyor means comprise a plurality of seats evenly distributed along the forming and feed line. The seats are designed to accept and retain a given quantity of the absorbent material; wherein the conveyor means comprise a continuous conveyor belt, which has at least one operating branch defining the forming and feed line. The operating branch extends along a straight path and moves at a given speed and in a given direction.

BRIEF DESCRIPTION OF THE DRAWINGS

The present invention is now described with reference to the accompanying drawings, which illustrate a preferred embodiment of the invention without limiting its scope of application and in which.

DESCRIPTION OF THE PREFERRED EMBODIMENTS

Figure 1:
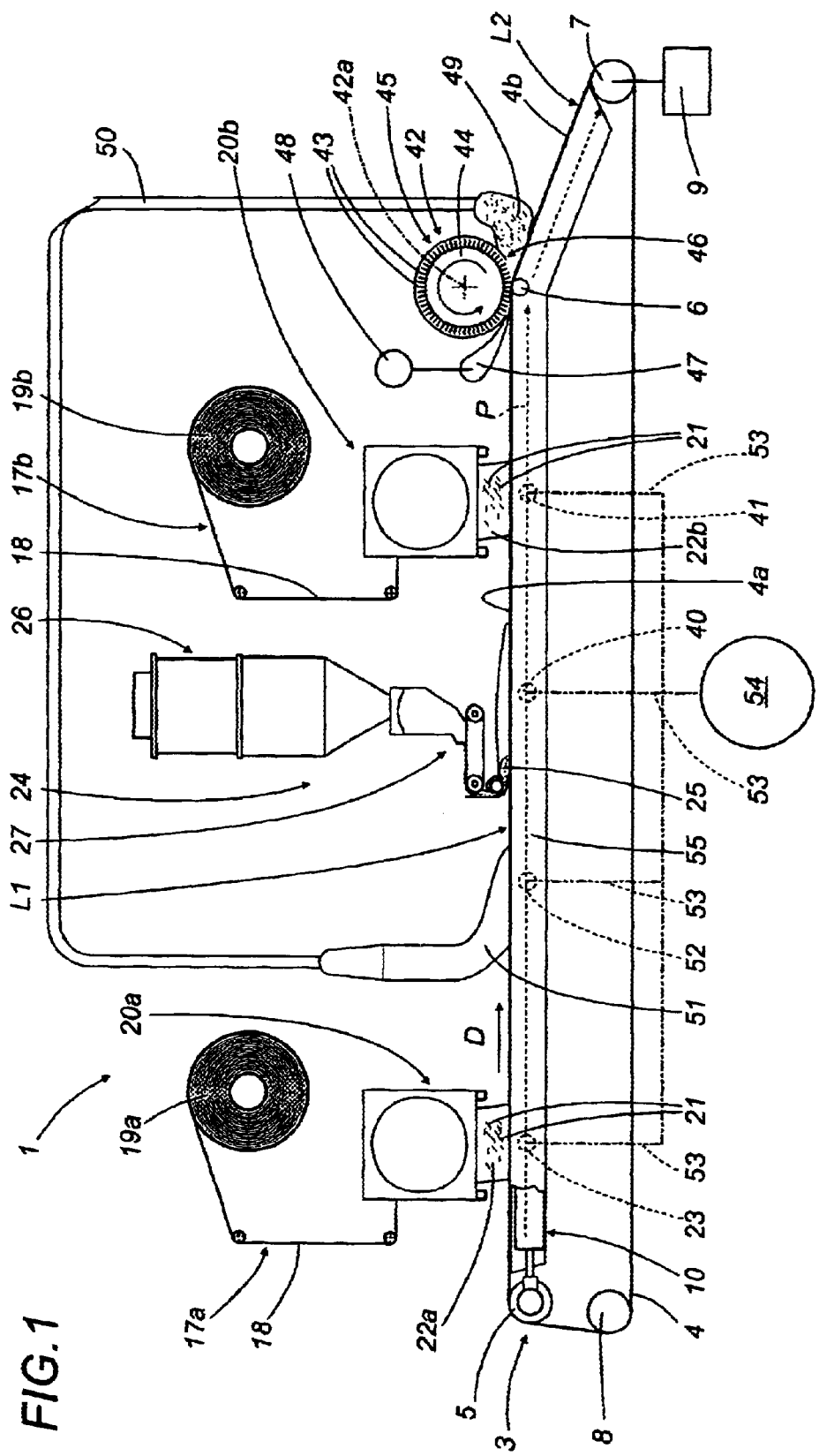
FIG. 1 is a schematic side view of a unit for making pre-shaped absorbent pads, in accordance with the present invention.
Figure 6:
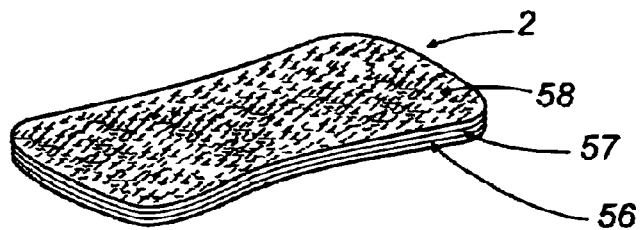
FIG. 6 is a perspective view of a pre-shaped diaper pad made by the unit in FIG. 1.

With reference to FIGS. 1 and 6, the numeral 1 indicates a unit for making pre-shaped and multi-layer absorbent pads 2 for sanitary items, in particular for diapers (not illustrated) as a whole.

The lower part of the unit 1 comprises a conveyor 3 which, in turn, comprises a continuous belt 4 closed in a loop over a plurality of pulleys 5, 6, 7 and 8 with a horizontal axis, one of which, pulley 7, is driven by a motor 9 so as to draw the belt 4 in a given direction D of feed.

Pulley 5 is connected to a tensioner 10 in order to maintain a given belt 4 tension.

Figure 3:
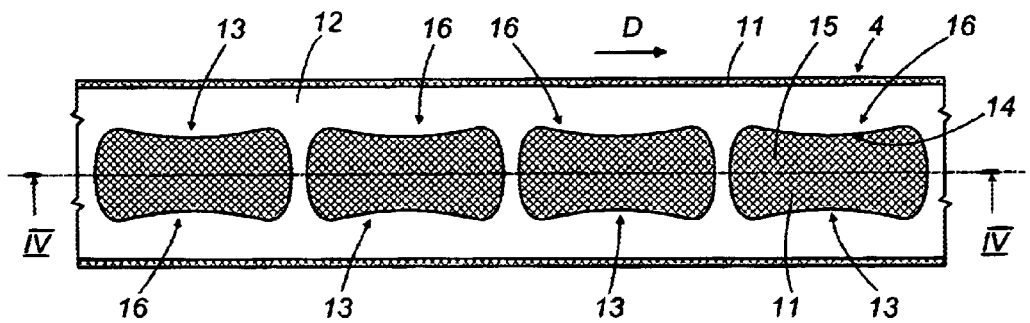
FIG. 3 is a plan view of another detail in FIG. 1.
Figure 4:
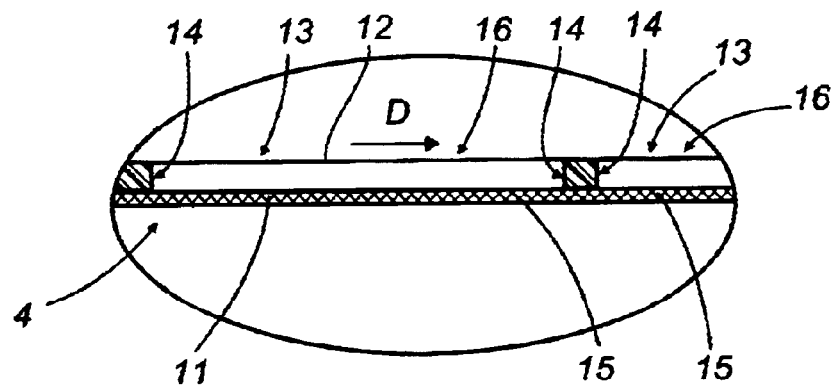
FIG. 4 is a cross-section along the line IV—IV in FIG. 3.
Figure 5:
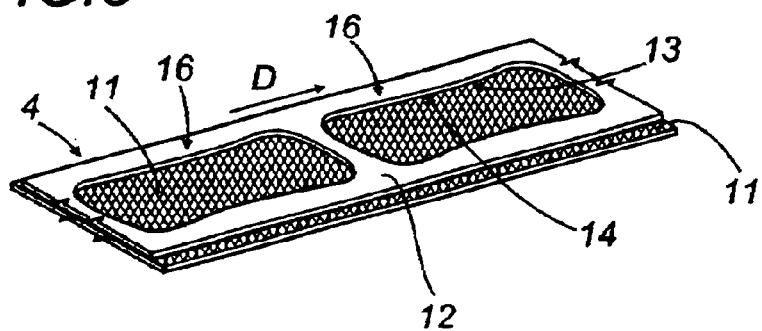
FIG. 5 is a perspective view of the detail in FIG. 3.

As is better illustrated in FIGS. 3, 4 and 5, the belt 4 consists of a metal mesh 11, on top of which a relatively thin layer 12 of a flexible material is joined, the material having a plurality of through-holes 13, the edge 14 of each defining the perimeter.

The edge 14 and a portion 15 of the metal mesh 11 delimited by the edge 14 respectively constitute a perimeter wall 14 and a base wall of a seat 16 for forming the pads 2.

The seats 16 are evenly distributed at constant intervals along the entire length of the belt 4.

Pulleys 5 and 6 together and on the belt 4 define an operating branch 4a defining a pad 2 forming and feed line L1. This branch 4a extends along a straight, horizontal path P and is mobile along the path P and in direction D at a given speed V.

Pulleys 6 and 7 together and on the belt 4 define a branch 4b which is angled downwards, defining a pad 2 outfeed line L2.

A first unit 17a which feeds a web of a first absorbent material 18, unwound from a reel 19a, is connected to a first mill 20a, of the known type, for breaking up the web into fibrous particles 21.

In particular, the above-mentioned web of first absorbent material 18 is a web of cellulose.

The mill 20a unloads the fibrous particles 21 onto the operating branch 4a of the belt 4 through a first pipe 22a, opposite which, on the other side of the belt 4, there is a first suction outlet 23.

Downstream of the mill 20a, in the above-mentioned direction D, there is a unit 24 which distributes a second absorbent material 25, consisting, in particular, of granules of a super-absorbent material of the known type.

The unit 24 comprises a storage tank 26 for the material 25 and a feeder device 27 for the material 25.

In particular, the feeder device 27 is located below the tank 26 and above the operating branch 4a.

Figure 2:
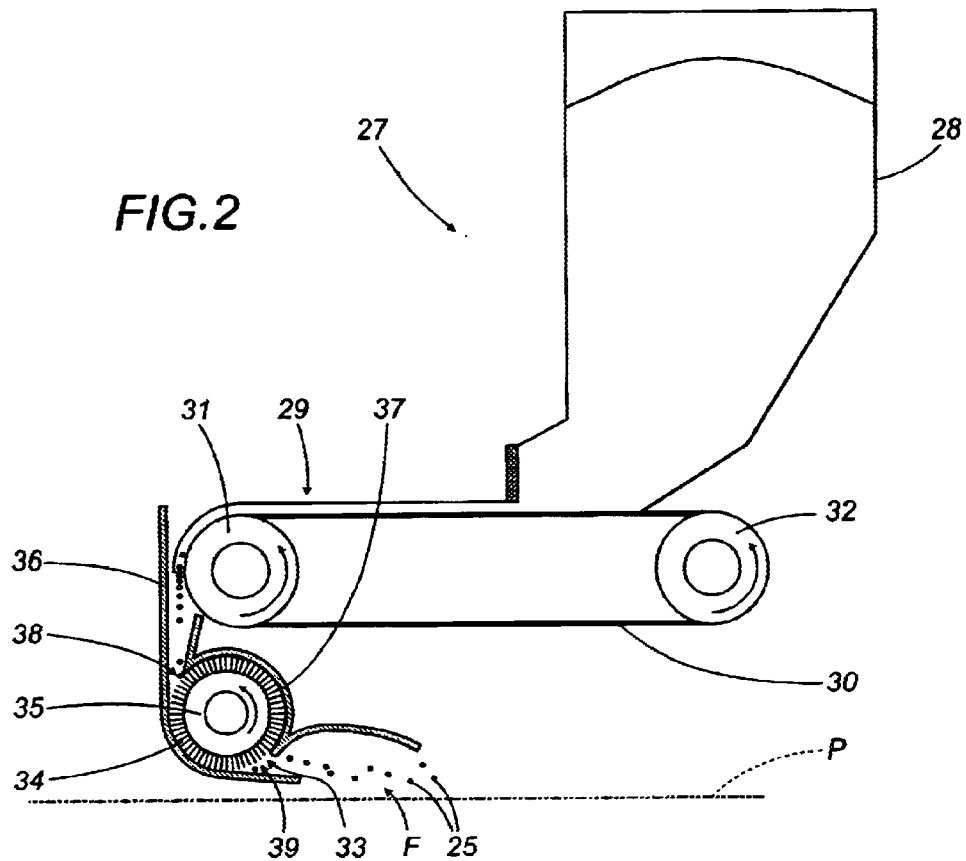
FIG. 2 is a side view of a detail in FIG. 1.

The feeder device 27, as is clearly illustrated in FIG. 2, comprises a hopper 28 which collects the second material 25 arriving from the tank 26 and a material 25 dosing device 29. The dosing device 29 comprises a conveyor belt 30 located below the hopper 28 and mobile on two pulleys 31 and 32 with a horizontal axis, one of which is driven by a motor of the known type which is not illustrated.

The feeder device 27 also comprises a material 25 accelerator brush 33, positioned below the dosing device 29 and designed to generate a flow F of granules of material 25 in substantially the same direction D and at the same feed speed V as the operating branch 4a.

The accelerator brush 33 comprises a plurality of accelerator elements 34 extending radially from the edge of a drum 35 with a horizontal axis, driven by a motor of the known type which is not illustrated. The brush 33 is partially surrounded by a first and a second containment and channeling wall 36 and 37, which define, for the brush 33, a feed zone 38 for the material 25 arriving from the conveyor belt 30 and an outfeed zone 39 for the flow F from the accelerator brush 33 to the operating branch 4a of the belt 4.

At the flow F outfeed zone 39, on the opposite side of the belt 4, there is a suction outlet 40.

Downstream of the distribution unit 24, in direction D, there is a second feed unit 17b for the above-mentioned web of first absorbent material 18, unwound from a reel 19b, which is connected to a second mill 20b, of the known type, for breaking up the web into fibrous particles 21.

Like the first mill 20a, the second mill 20b unloads the fibrous particles 21 onto the operating branch 4a of the belt 4 through a second pipe 22b, opposite which, on the other side of the belt 4, there is a suction outlet 41.

Downstream of the second mill 20b, in direction D, there is a rotary refining and cleaning brush 42, driven by a motor of the known type which is not illustrated and substantially at a tangent to the belt 4, in order to remove any excess particles of the materials 18 and 25 from the pad 2 forming seats 16.

The brush 42 rotates about a horizontal axis 42a along which it extends over the entire width of the belt 4. The brush 42 comprises a plurality of brushing elements 43 distributed on the edge of a drum 44, coaxial with the axis 42a. The edge is shaped by a circular containing wall 45, with the exception of a portion 46 opposite the operating branch 4a.

At this portion 46, the brush 42 operates together with an air-jet pipe 47, supplied by a compressed air source 48 and with an infeed end 49 of a recovery pipe 50, located on the opposite side of the pipe 47 relative to the brush 42.

On the opposite side to the infeed end 49, the recovery pipe 50 has a discharge outlet 51, which is located opposite the operating branch 4a in a position between the above-mentioned first mill 20a and distribution unit 24. On the opposite side of the belt 4 to the discharge outlet 51, there is a suction outlet 52.

The above-mentioned suction outlets 23, 40, 41 and 52 are connected, by relative pipes 53, to a suction well 54. The suction outlets 23, 40, 41 and 52 are also connected to one another by a shared suction manifold 55 below the belt 4, along the lines L1 and L2 and opposite the belt 4.

In practice, the motor 9 causes the pulley 7 to rotate. The pulley drives the belt 4 in direction D at the above-mentioned speed V.

During belt 4 feed, the seats 16 are fed along the forming and feed line L1, passing in succession beneath the first pipe 22a from the first mill 20a, where a first layer 56 of fibrous particles 21 of the first material 18 is deposited on the base 15 of each seat 16. The particles 21 are deposited on the base 15 following suction through the wall 15, which is permeable to air, originating from the vacuum created in the manifold 55 by the suction well 54. The methods with which the mill 20a breaks the absorbent material 18 into fibrous particles 21 and doses the particles 21 are known and, therefore, do not require explanation.

When it has left the first pipe 22a, each seat 16 is fed under the recovery pipe 50 discharge outlet 51, where the particles of material 18 and 25 removed by the brush 42 are deposited on the first layer 56.

Then, each seat 16 is fed under the outfeed zone 39 of the flow F of material 25 from the feeder device 27. The material 25 is deposited in the seat 16, depending on the quantity dosed by the conveyor belt 30, constituting a second layer 57 of absorbent material, on top of the first layer 56 and the particles of material 18 and 25 recovered using the pipe 50.

In particular, it should be noticed that the particles of material 25 which constitute the layer 57 are delicately placed in each seat 16 according to a flow F with substantially the same speed V and direction D of feed as the seat 16 itself.

Continuing along the forming and feed line L1, each seat 16 is positioned under the second pipe 22b from the second mill 20b, where a third layer 58 of fibrous particle 21 of the first material 18 is deposited on the second layer 57. Again, the methods with which the mill 20b breaks the absorbent material 18 into fibrous particles 21 and doses the particles 21 are known and, therefore, do not require explanation.

After leaving the pipe 22b, each seat 16 passes below the brush 42, which removes from the belt 4 any excess particles of material 18 and 25 projecting from the seat 16. In particular, it should be noticed that in addition to helping to recover the above-mentioned excess particles, the brush 42 also has a finishing function, which consists in leveling the third layer 58.

Finally, the seats 16, containing the completed pads 2, are fed along the outfeed line L2 towards an operating line which is not illustrated, along which, in a way that is known and therefore not illustrated, each seat 16 is closed between a permeable inner layer of spun-bound material and an impermeable outer layer of polyethylene, to form the relative diaper, which is not illustrated.

Obviously, the manifold 55 retains the absorbent material 18, 25 as it is deposited in the seats 16 along the length of the lines L1 and L2.

It is also obvious how the seats 16, together with the shape and thickness of the perimeter walls 14, give the pads 2 the desired shape.

Finally, it should be noticed that the walls 14 are extremely thin. As a result, the belt 4 is relatively thin and can be wound, without disadvantages, over pulleys 5, 6, 7 and 8 with relatively small diameters, having evident advantages in terms of the size of the conveyor 3.

What is claimed is:

1. A unit for making pre-shaped absorbent pads for sanitary items comprising: conveyor means comprising a continuous conveyor belt with at least one operating branch defining at least one forming and feed line for the absorbent pads, said operating branch extending along a straight path and being mobile at a given speed and in a given direction; the conveyor means comprising a plurality of seats evenly distributed along the forming and feed line and the seats being designed to accept and retain a given quantity of an absorbent material; a first and a second feed station located along the forming and feed line for feeding a first layer of a first absorbent material and a second layer of a second absorbent material into each seat; wherein the second feed station comprises feeder means for the second absorbent material, said feeder means comprising dosing means for the second absorbent material and accelerator means positioned at an outfeed of the dosing means and designed to feed the second absorbent material according to a flow with the same direction and feed speed as the operating branch.

2. The unit according to claim 1, comprising suction means located along the forming and feed line and connected to the seats; said suction means being designed to hold the absorbent material in the seats.

3. The unit according to claim 2, wherein the seats comprise a permeable base wall which can be made to communicate with the suction means, and a perimeter wall which co-operates with the base wall to keep the absorbent material in the seats and to give the absorbent pad a given shape and thickness.

4. The unit according to claim 1, comprising, along the forming and feed line, at least a third station for feeding the first absorbent material; the second feed station being positioned between the first and third feed stations.

5. The unit according to claim 1, comprising refining and cleaning means designed to remove excess particles of material from the seats.

6. The unit according to claim 5, comprising a circuit for recovering the particles of absorbent material; the infeed of the recovery circuit being connected to the refining and cleaning means, whilst the outfeed has a discharge outlet positioned along the forming and feed line.

7. The unit according to claim 2, comprising refining and cleaning means designed to remove excess particles of material from the seats.

8. The unit according to claim 3, comprising refining and cleaning means designed to remove excess particles of material from the seats.

9. The unit according to claim 4, comprising refining and cleaning means designed to remove excess particles of material from the seats.

10. The unit according to claim 7, comprising a circuit for recovering the particles of absorbent material; the infeed of the recovery circuit being connected to the refining and cleaning means, whilst the outfeed has a discharge outlet positioned along the forming and feed line.

11. The unit according to claim 8, comprising a circuit for recovering the particles of absorbent material; the infeed of the recovery circuit being connected to the refining and cleaning means, whilst the outfeed has a discharge outlet positioned along the forming and feed line.

12. The unit according to claim 9, comprising a circuit for recovering the particles of absorbent material; the infeed of the recovery circuit being connected to the refining and cleaning means, whilst the outfeed has a discharge outlet positioned along the forming and feed line.

\* \* \* \* \*